(12) United States Patent
Chakrabarti et al.

(10) Patent No.: US 6,949,368 B2
(45) Date of Patent: Sep. 27, 2005

(54) COMPOSITIONS AND METHODS FOR ENHANCING POLYNUCLEOTIDE AMPLIFICATION REACTIONS

(75) Inventors: Raj Chakrabarti, Princeton, NJ (US); Clarence E. Schutt, Princeton, NJ (US)

(73) Assignee: The Trustees of Princeton University, Princeton, NJ (US)

( * ) Notice: Subject to any disclaimer, the term of this patent is extended or adjusted under 35 U.S.C. 154(b) by 0 days.

(21) Appl. No.: 10/056,917

(22) Filed: Jan. 25, 2002

(65) Prior Publication Data

US 2003/0039992 A1 Feb. 27, 2003

Related U.S. Application Data

(60) Provisional application No. 60/264,935, filed on Jan. 30, 2001, provisional application No. 60/298,166, filed on Jun. 14, 2001, and provisional application No. 60/298,250, filed on Jun. 14, 2001.

(51) Int. Cl.[7] .......................... C12P 19/34; C07H 21/00; C07H 21/02
(52) U.S. Cl. .................... 435/91.2; 536/22.1; 536/23.1; 514/44
(58) Field of Search .............................. 536/23.1, 22.1; 435/91.2; 514/44

(56) References Cited

U.S. PATENT DOCUMENTS

| | | | | |
|---|---|---|---|---|
| 5,512,462 | A | * | 4/1996 | Cheng ........................ 435/91.2 |
| 5,545,539 | A | | 8/1996 | Miller ........................ 435/91.2 |
| 5,846,716 | A | | 12/1998 | Miller ............................ 435/6 |
| 6,114,150 | A | | 9/2000 | Weissman et al. .......... 435/91.2 |
| 6,261,773 | B1 | | 7/2001 | Segawa et al. ................. 435/6 |
| 6,300,075 | B1 | | 10/2001 | Preston et al. .................. 435/6 |
| 6,348,583 | B1 | * | 2/2002 | Segev ....................... 536/23.1 |

OTHER PUBLICATIONS

Ausubel, et al., "The Polymerase Chain Reaction" *Current Protocols in Molecular Biology*, Chapter 15, John Wiley & Sons, Inc., 2001, 15.01–15.1.14.
Baskaran, N. et al., "Uniform amplification of a mixture of deoxyribonucleic acids with varying GC content", *Genome Methods*, 1996, 6, 633–638.
McDowell, D.G. et al., "Localised sequence regions possessing high melting temperatures prevent the amplification of a DNA mimic in competitive PCR", *Nucl. Acids Res.*, 1998, 26, 3340–3347.
Newton & Graham, *PCR. Bios Scientific*, Oxford, 1994.
Roux, in: Dieffenbach & Dveksler, eds., "Optimization and Troubleshooting in PCR" *PCR Primer–A Laboratory Manual*. Cold Spring Harbor Laboratory Press, 1995, Cold Spring Harbor, NY, pp 53–61.
Smith, K.T. et al., "Using Cosolvents to Enhance PCR Amplification", *Amplifications*, 1990, 5, 16–17.
Varadaraj K. et al., "Denaturants or cosolvents improve the specificity of PCR amplification of a G + C–rich DNA using genetically engineered DNA polymerases", *Gene*, 1994, 140, 1–5.
Weissensteiner T. et al., "Strategy for controlling preferential amplification and avoiding false negatives in PCR typing", *BioTechniques*, 1996, 21, 1102–1108.
Winship, P.R., "An improved method for directly sequencing PCR amplified material using dimethyl sulphoxide", *Nucl. Acids. Res.*, 1989, 17, 1266.

(Continued)

*Primary Examiner*—Jezia Riley
(74) *Attorney, Agent, or Firm*—Ethan D. Civan

(57) ABSTRACT

Compositions and methods for enhancing PCR and other polynucleotide replication reactions are disclosed. These comprise the addition of low molecular weight organic amides, sulfones or sulfoxides to PCR or other replication reaction mixtures.

30 Claims, 4 Drawing Sheets

OTHER PUBLICATIONS

PCT International Search Report dated Jan. 31, 2003 (PCT/US02/02068).

Chakrabarti, R., et al., "The enhancement of PCR amplification by low molecular–weight sulfones," *Gene*, 2001, 274, 293–298.

Chakrabarti, R., et al., "The enhancement of PCR amplification by low molecular weight amides," *Nucleic Acids Research*, XP–002226382, 2001, 29(11), 2377–2381.

* cited by examiner

Endocyclic amides

δ-Valerolactam

ε-Caprolactam

2-Azacyclooctanone

2-Azacyclononanone

Exocyclic amides

N-formyl pyrrolidine

N-formyl piperidine

N-formyl morpholine

N-acetyl morpholine

Pyrrolidones 2-pyrrolidone   N-methylpyrrolidone (NMP)   N-hydroxyethylpyrrolidone (HEP)

Formamides

N-methylformamide (MMF)   N,N-dimethylformamide (DMF)

Acetamides

N-methylacetamide (MMA)   N,N-dimethylacetamide (DMA)

Higher-chain primary amides propionamide   isobutyramide n-Alkyl sulfones

Methyl sulfone

Ethyl sulfone n-Propyl sulfone

Cyclic sulfones

Tetramethylene sulfone
(Sulfolane)

2,4-Dimethylsulfolane

Butadiene sulfone
(Sulfolene)

Methyl sulfoxide Methyl sec-butyl sulfoxide n-Propyl sulfoxide n-Butyl sulfoxide Tetramethylene sulfoxide

COMPOSITIONS AND METHODS FOR ENHANCING POLYNUCLEOTIDE AMPLIFICATION REACTIONS

This application claims benefit under 35 U.S.C. §119(e)(1) to U.S. Provisional Application Nos. 60/264,935, filed Jan. 30, 2001, 60/298,166, filed Jun. 14, 2001, and 60/298,250, filed Jun. 14, 2001, the entireties of all of which are incorporated by reference herein.

Pursuant to 35 U.S.C. §202(c), it is acknowledged that the U.S. Government has certain rights in the invention described herein, which was made in part with funds from the National Science Foundation and the National Institutes of Health, Grant No. GM 44038.

FIELD OF THE INVENTION

The present invention relates to methods in molecular biology. In particular, the invention provides compositions and methods for enhancing polynucleotide amplification reactions.

BACKGROUND OF THE INVENTION

Various scientific articles, patents and other publications are referred to throughout the specification. Each of these publications is incorporated by reference herein in its entirety.

Polynucleotide amplification reactions have become central techniques of molecular biology. Indeed, many current methods in molecular biology utilize as their first step an amplification reaction involving either DNA or RNA as a template.

The polymerase chain reaction (PCR) and related techniques, such as NASBA (nucleic acid sequence-based amplification), TAS (transcription-based amplification system), 3SR (self-sustained sequence replication), LAR (ligation amplification reaction, Q-beta replicase and LCR (ligase chain reaction) are all methods of polynucleotide amplification. Many of these amplification reactions utilize a polymerase enzyme or fragment of such an enzyme.

Despite their widespread use, however, these techniques are often fraught with difficulties. In many cases, the standard procedure fails to produce meaningful amplification or any amplification at all. In other instances, the amplification of the target sequence is nonspecific, meaning that its amplification is accompanied by similar amplification of non-target polynucleotide fragments (Roux, 1995, in: Dieffenbach & Dveksler, eds., PCR Primer-A Laboratory Manual. Cold Spring Harbor Laboratory Press, Cold Spring Harbor, N.Y., pp. 55–66; Newton & Graham, 1994, PCR. Bios Scientific, Oxford). These problems, especially low yield, can be particularly severe for templates with high GC contents (Varadaraj & Skinner, 1994, Gene 140, 1–5; McDowell et al., 1998, Nucl. Acids Res. 26, 3340–3347).

Accordingly, improvement of amplification and stringency has been the focus of many research efforts. It has been found that various organic additives can often yield significant improvements in this regard, the most successful of the additives tested being DMSO, glycerol, polyethylene glycol, betaine and formamide (Winship, 1989, Nucl. Acids. Res. 17, 1266; Smith et al., 1990 Amplifications 5, 16–17; Weissensteiner & Lanchbury, 1996, BioTechniques 21, 1102–1108).

U.S. Pat. Nos. 5,545,539 and 5,846,716 to Miller et al. disclose a method for improving sequencing or amplification of polynucleotides that comprises including a glycine-based osmolyte, such as trimethylglycine, in the amplification or sequencing reaction mixture. Addition of this reagent was reported to be particularly advantageous in reducing the appearance of stutter bands in the amplification product.

U.S. Pat. No. 6,114,150 to Weissman et al. discloses methods and compositions for obtaining uniform amplification of nucleic acid templates with variable G+C content by adding to the reaction mixture a zwitterion and a compound that disrupts base pairing. Compounds such as betaine, monomethyl glycine, dimethylglycine and D-carnitine are disclosed as useful zwitterions; DMSO and formamide are disclosed as useful for disrupting base-pairing.

U.S. Pat. No. 6,300,075 to Preston et al. discloses a method to amplify nucleic acids that is alleged to improve the specificity of amplification of a target nucleic acid. The method comprises supplementing an amplification reaction mixture with a carrier nucleic acid and one or more magnesium salts. Addition of these materials is reported to reduce polymerase extension of non-target nucleic acids during amplification assays through a reduction in the amount of primer-dimer formation prior to raising the temperature of the amplification mixture during thermal cycling.

U.S. Pat. No. 6,261,773 to Segawa et al. discloses that the sensitivity of amplification reactions, particularly of RNA templates, may be improved by adding EDTA or a similar reagent, such as nitriotriacetic acid (NTA), uramil diacetic acid (UDA), trans-1,2-cyclohexanediaminetetraacetic acid (CyDTA), diethylenetriamine-pentaacetic acid (DTPA), ethyleneglycolbis(2-aminoethyl)ether diaminetetraacetic acid (GEDTA) or triethylenetetraminehexaacetic acid (TTHA), or salts thereof, to the reaction mixture. These compounds are reported to improve the signal-to-noise ratio of amplification reactions by significantly inhibiting the occurrence of non-specific amplification reactions.

Despite their general applicability, the performance of the currently available compounds, especially in the case of GC-rich targets, is quite unpredictable. Any given compound often fails to provide adequate improvement over the control (Baskaran et al., 1996, Genome Methods 6, 633–638).

Thus, increasing the selection of additives that are capable of improving polynucleotide amplification, especially for recalcitrant targets, would be a significant advance in the art of nucleic acid amplification. Such new additives would be of particular benefit by improving both the potency and specificity of the amplification reaction.

SUMMARY OF THE INVENTION

The present invention is drawn to compositions and methods for enhancing PCR and other polynucleotide replication reactions. The compositions comprise polynucleotide amplification reaction mixtures containing low molecular weight organic compounds as described below. The use of these compositions enables production of multiple copies of target genes or other nucleic acid sequences with high yield and specificity. The compositions offer the particular advantage of increased specificity and yield in the amplification of GC-rich targets, which are otherwise difficult to amplify.

According to one aspect of the invention composition for performing a polynucleotide replication reaction is provided, which comprises a buffer, one or more template polynucleotides, nucleotide triphosphates, one or more poly merase enzymes or fragments thereof, and one or more reaction adjuvants comprising compounds of the formula:

Formula I

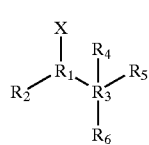

wherein:
$R_1$ is C or S; and
when $R_1$ is C, X is =O, $R_3$ is N and $R_6$ is absent;
when $R_1$ is S, X is =O or

and $R_3$ is C;
$R_2$ is H or $CH_3$ only when one or more of $R_4$, $R_5$ and $R_6$ is not H, and otherwise $R_2$ is an unsubstituted or halogen-, hydroxy- or alkoxy-substituted alkyl or cycloalkyl of length m, wherein m is selected such that the total number of carbons in the compound is between 3 and 8 when $R_1$ is C and between 2 and 8 when $R_1$ is S;
wherein any two of $R_2$, $R_3$, $R_4$, $R_5$ and $R_6$ optionally form a cyclic structure in which cyclization is effected through a bond between them; and
$R_4$, $R_5$ and $R_6$ each is H, alkyl, cycloalkyl or halogen-, hydroxy- or alkoxy-substituted alkyl or cycloalkyl of length n, wherein n is selected such that the total number of carbons in the compound is between 3 and 8 when $R_1$ is C and between 2 and 8 when $R_1$ is S.

In one embodiment, the reaction adjuvant is a cyclic compound, wherein the cyclization is effected through a bond between any two of $R_2$, $R_3$, $R_4$, $R_5$ and $R_6$. Preferably, the cyclic portion of the compound comprises five, six or seven members. In certain embodiments, the reaction adjuvants are amides, i.e., $R_1$ is C, X is =O, $R_3$ is N and $R_6$ is absent. Preferred examples of cyclic forms of amides include 2-pyrrolidone, N-methylpyrrolidone and N-hydroxyethyl pyrrolidone, δ-valerolactam, ε-caprolactam and N-formyl morpholine. Preferred examples of acyclic forms of amides include propionamide and N,N-dimethyl acetamide.

In other embodiments, the reaction adjuvant is a sulfone or sulfoxide, i.e., it comprises a compound of Formula I in which $R_1$ is S, X is =O or

, and $R_3$ is C. Preferred examples of cyclic forms of these compounds include tetramethylene sulfone and tetramethylene sulfoxide. Preferred examples of acyclic forms of these compounds include methyl sulfone, ethyl sulfone, n-propyl sulfone, n-propyl sulfoxide and methyl sec-butyl sulfoxide.

In one embodiment, the reaction adjuvant has a potency of at least 75% of the potency of DMSO or formamide in an equivalent polynucleotide chain reaction (PCR). In another embodiment, the reaction adjuvant has a specificity of at least 80% of the specificity of DMSO or formamide in an equivalent polynucleotide chain reaction (PCR). In another embodiment, the reaction adjuvant has an effective range spanning at least 0.1 M.

According to another aspect of the invention, a method is provided for performing a polynucleotide replication reaction, which comprises performing the reaction in the presence of one or more reaction adjuvants as described above. In a preferred embodiment, the polynucleotide replication reaction is an amplification reaction, preferably polymerase chain reaction, nucleic acid sequence-based amplification, transcription-based amplification system, self-sustained sequence replication, ligation amplification reaction, Q-beta replicase amplification or ligase chain reaction. polymerases or fragments thereof suitable for use in the method include Taq polymerase, Tth polymerase, Tme polymerase, Tli polymerase, Pfu polymerase, DNA polymerase I, Klenow fragment and reverse transcriptase.

The present invention also provides kits for performing a polynucleotide replication reaction. The kits comprise one or more of the reaction adjuvants described above, along with instructions for using the one or more compounds in a polynucleotide replication reaction. Optionally, the kits may further comprise one or more of: (a) a polynucleotide replication reaction buffer; (b) nucleotide triphosphates; (c) oligonucleotide primers; (d) a known template polynucleotide for us as a control; or (e) one or more polymerase enzymes.

According to yet another aspect of the invention, a method is provided for optimizing a polynucleotide replication reaction for a selected polynucleotide. The method comprises the steps of: (a) providing a plurality of reaction adjuvants as described above; (b) performing a plurality of polynucleotide replication reactions on the selected polynucleotide, each reaction being performed under equivalent conditions, but with varying type or amount of the reaction adjuvants in the reactions; and (c) selecting the type and concentration of reaction adjuvant that yields the most favorable results for polynucleotide replication of the selected polynucleotide template, thereby optimizing the polynucleotide replication reaction for the selected polynucleotide template. Kits for performing this method are also featured.

Other features and advantages of the invention will be understood by reference to the drawings, detailed description and examples that follow.

DETAILED DESCRIPTION OF THE INVENTION

Figure 1:
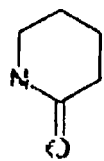
FIG. 1. Structures of certain cyclic amide compounds of Formula I.
Figure 1:
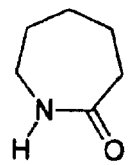
Figure 1:
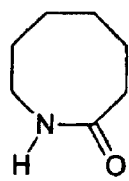
Figure 1:
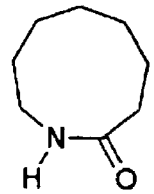
Figure 1:
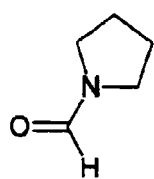
Figure 1:
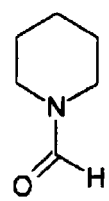
Figure 1:
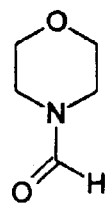
Figure 1:

As used herein, the term "polynucleotide replication" (PR) refers to any reaction in which a second strand of a nucleic acid molecule is synthesized using a first strand as a template. These PR reactions generally encompass amplification of the template polynucleotide, as with PCR and related methods, or cDNA synthesis from an RNA template using reverse transcriptase (RT). Thus the terms "polynucleotide amplification" (PA) or "nucleic acid amplification" are also used herein to describe such PR reactions.

A typical PR reaction mix contains a polymerase or fragment thereof or combination of polymerases having specified activity, dNTPs, a template polynucleotide (DNA or RNA), oligonucleotide primers (in most reactions), an appropriate reaction buffer (e.g., Tris-HCl, with $MgCl_2$, for Taq DNA polymerase) and various additives to enhance the amplification of the template polynucleotide. Additives currently in use include formamide, DMSO, betaine, polyethylene glycol, glycerol, tetramethylammonium chloride and certain nonionic surfactants such as Tween 20.

In accordance with the present invention, a variety of new PR reaction additives have been identified. These compounds have been found superior to currently-used additives for enhancing polynucleotide amplification.

Three criteria are used to determine if a particular additive is advantageous: high potency, high specificity and a wide effective range. When results are viewed as bands of electrophoresed amplification products, potency is defined as the maximum densitometric volume of the target band observed at any concentration of an additive. Specificity is defined as the ratio of target band volume to the total volume of all bands, including nonspecific bands, usually expressed as a percentage. The effective range of an additive is defined as the range of concentrations over which the volume of target band amplification is greater than or equal to 50% of its maximum value.

The inventors assessed numerous compounds for their ability to enhance the potency and specificity of polynucleotide amplification reactions, at a useful effective range. Three classes of compounds were assessed in detail low molecular-weight amides, sulfoxides and sulfones. As discussed in greater detail below, several of these compounds proved superior to current additives. Notably though, certain members of each class of compounds proved particularly effective, namely 2-pyrrolidone and formyl morpholine in the amide class, sulfolane in the sulfone class and tetramethylene sulfoxide in the sulfoxide class. These members were found to share structural features that could account for their particular effectiveness. One structural feature shared by the most effective compounds is that they are cyclic, with one component of the ring structure being N or S.

It is known that organic solvents that enhance PCR and other amplification reactions can also unwind the DNA double helix. For this reason, it has been proposed that organic additives such as formamide exert their effect in amplification reactions by binding in the major and minor grooves of DNA and destabilizing the template double helix. Without intending to be limited by any explanation as to mechanism of action, the superior performance of the aforementioned cyclic compounds over their acyclic counterparts may in part be due to a greater affinity of the cyclic compounds for grooves of the double stranded template. The cyclic structure may constrain the molecules in a conformation that is optimal for complementary hydrogen bonding with donor and acceptor components in the major and minor grooves. It may also minimize steric repulsion with neighboring groups on the DNA backbone by restricting free rotation.

From the work on sulfones described in Example 2, data suggested that multiple additive molecules pack into the major grooves of DNA. The fact that propyl and methyl sec-butyl sulfoxide are effective at especially low concentrations (Example 3) may also be linked to the phenomenon of packing. The longer carbon chains of these compounds could create a hydrophobic environment in the grooves that facilitates the binding of other additive molecules, especially at lower concentrations. This sort of packing would bear a resemblance to micellar or hemimicellar structures often formed by surfactants at low concentrations. Methyl-long chain alkyl sulfoxides have been shown to form such structures quite stably; this may explain in part the lower effective concentration and greater potency of methyl sec butyl sufoxide compared to propyl sulfoxide.

In the experiments on sulfones described in Example 2, the superior potency of methyl sulfone compared to DMSO was demonstrated, noting that, while the individual sulfone oxygens may hydrogen bond less strongly than a sulfoxide oxygen, the overall bonding is likely stronger for sulfones, provided that the oxygens are oriented favorably. The fact that the higher alkyl sulfones (ethyl and propyl) are less potent in amplification enhancement than the higher alkyl sulfoxides (methyl sec-butyl and propyl) (Example 3) might be the result of an inability of the higher sulfones to bond effectively with both oxygens within the packing constraints imposed by the major groove architecture. The significant steric bulk of butyl sulfoxide may render it less capable, or incapable, of packing.

A similar effect could be responsible for the greater potency of tetramethylene sulfoxide compared to sulfolane (Example 3). As mentioned, the ring structures of these molecules are most likely constrained by groove architecture in such a way that the oxygens face directly toward the hydrogen bond donors in the grooves. In the case of sulfolane, the oxygens are fixed in such a configuration above and below the plane of the base pair. This probably results in weaker hydrogen bonding compared to tetramethylene sulfoxide, where the oxygen would project directly toward the H-bond donors. The smaller effective range of sulfolane may be attributable to the phenomenon described above for ethyl and propyl sulfones, i.e., sulfolane may be less capable of effectively bonding with both oxygens at higher packing concentrations within the major groove.

The extra H-bond in G:C base pairs compared to A:T base pairs faces the minor groove. The significant geometric constraints of the minor groove might make it difficult for longer straight-chain molecules to bond there. The cyclic structure of tetramethylene sulfoxide and sulfolane, however, may fit perfectly into the minor groove architecture, and remain there stably due to van der Waals interactions with neighboring groups on the DNA backbone. This would be expected to position the oxygens on the compounds in orientations that are highly conducive to effective hydrogen bonding. This model predicts that as template GC content increases, the effectiveness of additives that are incapable of hydrogen bonding in the minor grooves should decrease. Indeed, as shown, propyl sulfoxide is completely ineffective with PSM, the most GC-rich template used (73% GC 158 bp region), and is only marginally effective with c-jun (64% GC). However, as can be seen from Table 8 (Example 3), both propyl and methyl sec-butyl sulfoxides are more effective than the smaller additives DMSO and methyl sulfone for the lower GC content template GTP (58% GC). The higher acyclic sulfones and sulfoxides may destabilize A:T base pairs as well if not better than DMSO and methyl sulfone due to the fact that the H-bond donors in A:T pairs all face the major groove, where the higher sulfones and sulfoxides may engage in efficient hydrophobic packing.

Thus, based on the experimental evidence generated in accordance with the present invention, it has been determined that certain low molecular weight compounds are particularly effective in the enhancement of polynucleotide amplification reactions. These compounds are described by the general Formula I:

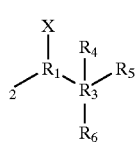

Formula I wherein:

$R_1$ is C or S;
when $R_1$ is C, X is =O, $R_3$ is N and $R_6$ is absent;
when $R_1$ is S, X is =O or

and $R_3$ is C;

$R_2$ is H or $CH_3$ only when one or more of $R_4$, $R_5$ and $R_6$ is not H, and otherwise $R_2$ is an unsubstituted or halogen-, hydroxy- or alkoxy-substituted alkyl or cycloalkyl of length m, wherein m is selected such that the total number of carbons in the compound is between 3 and 8 when $R_1$ is C and between 2 and 8 when $R_1$ is S, wherein any two of $R_2$, $R_3$, $R_4$, $R_5$ and $R_6$ can be part of a cyclic structure in which cyclization is effected through a bond between them; $R_4$, $R_5$ and $R_6$ each is H, alkyl, cycloalkyl or halogen-, hydroxy- or alkoxy-substituted alkyl or cycloalkyl of length n, wherein n is selected such that the total number of carbons in the compound is between 3 and 8 when $R_1$ is C and between 2 and 8 when $R_1$ is S.

Compounds of this general formula comprise the size, charge and steric features that enable them to facilitate unwinding of double stranded polynuclotides and retardation/prevention of secondary structure formation in single stranded molecules. Furthermore, these compounds are more potent than those currently available, and so can be used effectively at lower concentrations. At their effective concentrations, these compounds are substantially benign toward polymerases and other enzymes used in amplification reactions.

Within Formula I, certain compounds have been found particularly effective in enhancing polynucleotide amplification, particularly of recalcitrant polynucleotides, such as those with high GC content. Thus, in preferred embodiments, the compound is a cyclic compound wherein the cyclization is effected through a bond between any two of $R_2$, $R_3$, $R_4$, $R_5$ and $R_6$. Particularly preferred are unsubstituted or minimally substituted compounds (except for the substitution on $R_1$) having a total ring size of five, six or seven members. When the compound is an amide ($R_1$ is C and $R_3$ is N) and cyclic, it is preferred that one of $R_4$ or $R_5$ is H or is no larger than methyl, ethyl or hydroxyethyl. When the compound is a sulfoxide or sulfone ($R_1$ is S) and cyclic, it is preferred that the remainder of the compound is completely unsubstituted.

While any compound of Formula I is considered within the scope of the present invention, exemplified herein are the particularly preferred low molecular weight amides, sulfones and sulfoxides.

Within the amide group, cyclic amides are preferred, as mentioned above, and may comprise compounds that are either endocyclic or exocyclic with respect to the amide carbon. Examples of endocyclic and exocyclic amides of Formula I are shown in FIG. 1. Compounds in which the cyclic structure is formed by a bond between $R_4$ and $R_5$ are called exocyclic amides. Compounds in which the cyclic structure is formed by a bond between $R_2$ and either $R_4$ or $R_5$ are called endocyclic amides. If the compound is endocyclic, then N may be unsubstituted (i.e., $R_4$ or $R_6$ is H) or substituted such that $R_4$ or $R_5$ are methyl or lower alkyl, or halogen-, hydroxy- or alkoxy-substituted lower alkyl, e.g., ethyl or hydroxy ethyl. Exemplary compounds of this category include, but are not limited to, 2-pyrrolidone, N-methylpyrrolidone and N-hydroxyethyl pyrrolidone, each of which is described in Example 1, as well as δ-valerolactam, ε-caprolactam and N-formyl morpholine.

Certain acyclic amides also have been found equal or superior to the formamide currently used in amplification reactions. These include acetamide and also compounds of Formula I wherein: (1) $R_2$ is H or methyl and one or both of $R_4$ and $R_5$ is methyl or lower alkyl (or halogen- hydroxy- or alkoxy-substituted lower alkyl); or (2) $R_2$ is lower alkyl (or halogen- hydroxy- or alkoxy-substituted lower alkyl). Exemplary compounds of this category include, but are not limited to, propionamide and N,N-dimethyl acetamide, each of which is described in Example 1.

Within the sulfones and sulfoxides, cyclic molecules are preferred, as discussed above, preferably having a ring size of five, six or seven members, which is largely or completely unsubstituted with the exception of the sulfoxide or sulfone oxygens. Exemplary compounds of this category include, but are not limited to, tetramethylene sulfone and tetramethylene sulfoxide, which are described in Example 2 and Example 3, respectively.

Certain acyclic sulfones and sulfoxides also have been found equal or superior to currently used additives, e.g., formamide, DMSO, betaine. These are preferably compounds of Formula I wherein $R_2$ or $R_3$, or both, are short alkyl or substituted alkyl groups, e.g., ethyl, sec-butyl or propyl. Exemplary compounds of this catgory include, but are not limited to, methyl sulfone, ethyl sulfone, n-propyl sulfone, n-propyl sulfoxide and methyl sec-butyl sulfoxide, which are described in Example 2 and Example 3.

The effectiveness of a compound of the invention to enhance polynucleotide amplification is assessed under defined conditions. Though the compounds are useful for any type of amplification reaction, they are assessed using PCR reactionsunder the following conditions. One or more of three standard templates are used: a 996 bp segment of human myeloid leukocyte c-jun cDNA, a 511 bp segment of human prostate-specific membrane antigen (PSM) cDNA, and bovine brain glycolipid transfer protein (GTP) cDNA (660 bp), Following PCR, reaction products are separated, e.g., via agarose gel electrophoresis, and quantified using three mesurable parameters: (1) potency, defined as the maximum densitometric volume of the target product at any concentration of the compound; (2) specificity, defined as the ratio of the target product volume to the total volume of all reaction products (usually expressed as a percent); and (3) effective range, defined as the range of concentrations of the compound in which amplification of the target sequence is at least 50% of its maximum value. These values may be normalized to a "standard" compound currently used as a polynucleotide amplification reaction additive, e.g., formamide or DMSO.

Using these parameters, a compound of Formula I is considered suitable for use as an enhancer of polynucleotide amplification when it has a potency of at least 75%, preferably 125% and most preferably 200% compared with either DMSO or formamide for at least one of the three DNA fragments. It is further preferable that the compound have a specificity of at least 80%, preferably 90% and most preferably 95% for either GTP or PSM. Finally, the compound preferably has an effective range that spans a minimum interval of 0.1M, i.e., the difference between the upper and lower concentrations in the effective range is at least 0.1M, for instance 0.4–0.5M or 0.6–0.7M. Broader effective ranges, e.g., 0.15M, 0.2M, 0.25M, 0.3M or beyond may be useful and preferable. However, if a particular reagent demonstrates superior qualities of potency and specificity, its effective range, even if as narrow as, or narrower than, the minimum preferred range of 0.1M, is of lesser importance.

The compounds of Formula I can be used to enhance synthesis and amplification of any polynucleotide template, including DNA and RNA. They are particularly useful for amplification of polynucleotides with high GC content or regions of secondary structure. In amplification reactions such as PCR, addition of the compounds increases the efficiency of polynucleotide synthesis per round of amplification, especially for GC rich templates. This is of significance because even a slight decrease in efficiency in a single cycle (e.g., 10%) can lead to a large decrease in total product, e.g., 95%. High secondary structure of templates causes pausing and dissociation of the polymerase from the template, leading to non-specific amplification products. The compounds of Formula I decrease secondary structure of templates, thereby increasing specificity.

Compounds of Formula I are useful as additives in any PR reaction. These include amplification reactions such as PCR, NASBA (nucleic acid sequence-based amplification), TAS (transcription-based amplification system), 3SR (self-sustained sequence replication, LAR (ligation amplification reaction, Q-beta replicase and LCR (ligase chain reaction). In fact, any polymerase-based reaction involving a template that requires denaturing, e.g., a double stranded template or a single-stranded template with secondary structure, will be facilitated by addition of a compound of Formula I. For instance, in addition to the above amplification reactions, the compounds can facilitate reverse transcriptase (RT) reactions involving RNA templates with secondary structure. Additional specific uses of these compounds for polynucleotide synthesis and amplification are described in greater detail later in this section.

It should be noted that any molecular biology technique that incorporates polynucleotide denaturation as a step may be improved by the addition of a compound of Formula I to enhance denaturing, in a manner similar to the way formamide is currently used. However, reactions that utilize a polymerase or other enzyme require compounds that are more than simply good denaturants: the compounds also must be benign toward the enzymes. As an illustration, urea is a very good denaturant but inhibits polynucleotide amplification reactions because it damages polymerase enzymes. The compounds of Formula I are generally more potent than formamide and therefore can be used at lower concentrations. These compounds have a discemable effective range as described herein. The upper delimitation of this range relates in part to inactivation of polymerases at higher concentrations of the compounds.

Thus, the compounds of Formula I are used to best advantage in PR reactions that utilize a polymerase or derivative or fragment thereof, alone or in combination with one another or with other enzymes. In a preferred embodiment, the PR reaction is an amplification reaction. In a particularly preferred embodiment, it is a PCR. One aspect of the present invention features an amplification reaction mixture, preferably a PCR mixture, comprising the following ingredients: a polymerase, a template polynucleotide, dNTPs, oligonucleotide primers (in most applications; one exception is RT reactions where the synthesis of DNA is self-priming), a reaction buffer, and one or more enhancing agents (also referred to herein as "reaction adjuvants") comprising compounds of formula I.

In thermocycling amplification reactions, the polymerase may be a thermostable polymerase, including but not limited to Taq, Tth, Tme, Tli, and Pfu polymerases or variants thereof. In reactions that do not involve thermocycling, the polymerases may be DNA polymerase I, Klenow fragment or a reverse transcriptase. Combinations of polymerases include, for example, combinations in which one polymerase lacks a 3'-5' exonuclease activity (proofreading) and another possesses the activity.

Other ingredients of the reaction mixture are well described in the art, for instance, Ausubel et al., Current Protocols in Molecular Biology, John Wiley & Sons, Inc., 2001, and the Examples herein. The template polynucleotide may be single or double-stranded DNA, RNA or heterologous DNA-RNA double strands. Preferably, the template is a sequence between about 50 and 35,000 bases, and can be from various sources, including but not limited to genomic DNA, cDNA, plasmid DNA, viral DNA, DNA fragments and RNA, as mentioned above.

In reactions utilizing added oligonucleotide primers, preparation and use of such primers is well known in the art. Primers preferably are between about 10 and 30 bases in length. Multiple primers may be added to a single reaction mixture to prime multiple templates or multiple sites on a single template. Such multiplex amplification results in the simultaneous amplification of several targets.

The reaction buffer and additional reaction reagents utilized in PR reactions are well known in the art.

Enhancing agents comprising compounds of Formula I are added to the reaction mixture at a concentration deemed to be within the effective range of the particular agent, determined by calculation in a reference amplification reaction as described above and in the Examples (effective range calculated as a concentration yielding amplification of the target sequence of at least 50% of the maximum amount achievable by the agent). In a preferred embodiment, the concentration of a selected agent in a reaction mixture is near the peak of its most effective concentration, i.e., yielding amplification of the target sequence of at least 60%, more preferably, 70%, yet more preferably 80%, even more preferably 90%, and most preferably at 100% of the maximum value achievable by the agent for a selected template.

Once the reaction mixture is assembled, polynucleotide synthesis or amplification is conducted according to methods established for the particular reaction being performed. It will be appreciated by one of skill in the art that such methods are subject to variation and optimization depending upon the type of synthesis/amplification reaction being performed, as well as the target polynucleotide being synthesized. Reaction products are assessed according to standard methods, and as described hereinabove and in the Examples.

In addition to the reaction mixtures and methods described herein, the present invention also includes kits that facilitate the use of PR-enhancing agents to synthesize a target polynucleotide. At minimum, such kits comprise containers that include one or more of the compounds of Formula I and instructions for their use in enhancing polynucleotide replication or amplification. Kits also may include one or more of the following components: (1) reaction buffers or other additives for a reaction mixture; (2) dNTPs; (3) oligonucleotide primers designed for use with one or more pre-determined target sequences; (4) a known template polynucleotide for use as a control; and (5) a polymerase enzyme.

It is well known that PCR or other amplification and replication of a particular target sequence may be optimized through the adjustment of reaction ingredients and conditions. The present inventors have identified a large number of compounds—many more than heretofore available—useful for enhancing PR reactions in general and for optimizing replication/amplification of a particular predetermined target. Thus, in addition to the kits described above, the present invention further provides kits for optimizing amplification/replication of one or more selected target polynucleotides. These kits comprise, at minimum, containers including two or more, preferably several, enhancing agents comprising compounds of Formula I and instructions on their use in PCR and other amplification/replication reactions. Reaction mixtures comprising the selected target sequence and various concentrations of the enhancing agents are assembled, the amplification reaction is performed and results are compared. In this manner, the best enhancing agent and the optimum concentration of that agent for the particular target sequence may be determined.

The compositions and methods described herein will find broad utility in any technique that employs polynucleotide replication or amplification. A non-exhaustive list of such applications is presented below:

1. Reverse-transcriptase PCR—PR-enhancing agents of the invention are useful in both steps; duplication of the mRNA template and PCR of the resulting cDNA.
2. Site-specific mutagenesis.
3. PCR-based labeling of oligonucleotides.
4. RACE (rapid amplification of cDNA ends).
5. Cloning/expression of DNA.

In particular, the following applications will be improved by the present invention.

6. Genomic sequencing: many genes have high GC content or occur in regions of the genome where GC content is high.
7. DNA computing, which uses an amplification step as a central component.
8. RT reactions on templates with secondary structure.
9. Denaturing Gradient Gel Electrophoresis (DGGE)—formamide is currently used, but many of the compounds of Formula I may be used at lower concentration.
10. Medical diagnostics involving amplification of low copy number sequences.
11. Quantitative PCR.
12. Amplification of tandem repeats in a genome.
13. In situ PCR.
14. Forensics where sample size is limited and copy number is low.

The following examples are provided to describe the invention in greater detail. They are intended to illustrate, not to limit, the invention.

EXAMPLE 1

Enhancement of Polynucleotide Amplification by Low Molecular Weight Amides

Formamide is one of the most widely used additives in polynucleotide amplification and other nucleic acid techniques in which strand denaturation or hybridization occurs. It has been particularly noted for its ability to improve specificity in PCR. It seemed possible that other amides could improve PCR amplification and specificity. This example describes the results of a comprehensive structure-activity investigation with a group of low molecular weight amides to see how variations in the amide structure influence PCR amplification and specificity.

We report below the results of this investigation, which included the following amides: formamide, N-methylformamide (MMF), N,N-dimethylformamide (DMF), 2-pyrrolidone, N-methylpyrrolidone (NMP), N-hydroxyethylpyrrolidone (HEP), acetamide, N-methylacetamide (MMA), N,N-dimethylacetamide (DMA), propionamide and isobutyramide. We identify a number of amides from this group that are novel and potent enhancers of PCR.

Materials and Methods

Amplification reactions were carried out under the following conditions: 10 mM Tris-HCl (pH 8.8), 50 mM KCl, 1.5 mM MgCl2, 0.01% (w/v) gelatin, 0.2 uM primers, 0.06 ng/ul template, 0.2 mM each dNTP, 0.04 U/ul Taq polymerase. The templates used were bovine brain N-WASP cDNA (1518 bp), a 996 bp segment of human myeloid leukocyte c-jun cDNA, a 511 bp segment of human prostate-specific membrane antigen (PSM) cDNA, and bovine brain glycolipid transfer protein (GTP) cDNA (660 bp). cDNA synthesis was carried out using the First-Strand RT-PCR kit from Stratagene on the respective mRNAs purchased from Clontech. All amplification reactions for each gene were carried out using a single master batch of cDNA. Taq polymerase and dNTPs were obtained from Stratagene. Primers were obtained from Genosys. Primer melting temperatures ($T_m$s) were calculated using the Genosys oligo calculator program. The sequences of the primers were as follows.

N-WASP primer n1: d(ATGAGCTCCGGCCAGCAGC) (SEQ ID NO: 1),
primer n2: d(TCAGTCTTCCCATTCATCATCATCCTC) (SEQ ID NO:2);
c-jun primer j1: d(ATGACTGCAAAGATGGAAACG) (SEQ ID NO: 3),
primer j2: d(TCAAAATGTTTGCAACTGCTG-CG) (SEQ ID NO:4);
PSM primer p1: d(AAACACTGCTGTGGTGGA) (SEQ ID NO:5),
primer p2: d(TAGCTCAAC-AGAATCCAGGC) (SEQ ID NO:6);
GTP primer g1: d(GAATTCGAAATGGCGCTGCTGG) (SEQ ID NO:7),
primer g2: d(CTCGAGGTCCAGAGTACCCGCTGTG) (SEQ ID NO: 8). Calculated $T_m$s of the primers were as follows: n1-72.4° C., n2-70.7° C., j1-63.9° C., j2-70.8° C., p1-60.3° C., p2-61.9° C., g1-73.3° C., g2-74.4° C.

Additive chemicals were obtained from the following sources. N-methylformamide, N,N-dimethylformamide, acetamide, N-methylacetamide, N,N-dimethylacetamide and propionamide were purchased from Acros. 2-pyrrolidone, N-hydroxyethylpyrrolidone and N-methylpyrrolidone were obtained as free samples from BASF Corporation. Isobutyramide was purchased from Aldrich. Formamide was purchased from Gibco-BRL.

Polymerase chain reactions for the N-WASP gene were conducted on a Robocycler Gradient 40 thermal cycler from Stratagene using 100 ul solutions in 600 ul thin-walled tubes. For expediency, amplification of c-jun, PSM and GTP was carried out in a Robocycler Gradient 96 thermal cycler from Stratagene using 50 ul solutions in 200 ul thin-walled tubes. Prior to Taq polymerase addition, a hotstart protocol was carried out that consisted of an initial cycle of 95° C. for 5 minutes (11) to ensure complete first-strand separation, followed by a cycle of 54° C. for 5 minutes. Amplifications were run for 30 cycles. Denaturation was done for 1 minute at the minimum temperatures that yielded discernable amplification: 92° C. for N-WASP and 95° C. for c-jun, PSM and GTP. Extension was done at 72° C. for periods depending on target length: 2 minutes for N-WASP, 1.5 minutes for c-jun and GTP, and 1 minute for PSM. Annealings were carried out either at fixed concentrations of additives using temperature gradients of 38–56° C. for N-WASP and 44–58° C. for the other targets, or at varying concentrations of additives using fixed temperatures of 41° C. for N-WASP, 50° C. for c-jun and PSM, and 54° C. for GTP.

Amplification products were analyzed by agarose gel electrophoresis on 0.8% agarose gels in which 20 ul reaction products were loaded with 4 ul loading buffer. Gels were stained with ethidium bromide, visualized on a UV transilluminator (Fisher), and documented by photography. Densitometric quantitation of amplification products was carried out using Image Scanner and Image Master software from Amersham Pharmacia. Background correction was done using the software's rolling disc method.

Results

The bovine brain N-WASP gene (1518 bp, 49% GC) was selected as the primary subject of this study because it offered a good opportunity to differentiate structure-activity correlations of additives. Under the conditions used, it failed to amplify to any meaningful extent in the absence of additives and in the presence of DMSO, one of the most widely used additives, PCR resulted in rather low amplification and poor specificity. Multiple low molecular weight bands appeared in the latter case. Various concentrations of DMSO were tested using an annealing temperature gradient of 38–56° C.; 5% concentration gave the best results, which were nonetheless unsatisfactory.

Figure 2:
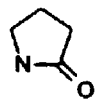
FIG. 2. Structures of certain amides tested for enhancement of polymerase chain reaction, as described in Example 1. Abbreviations used herein are indicated in parentheses.
Figure 2:
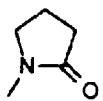
Figure 2:
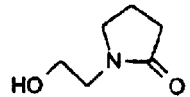
Figure 2:
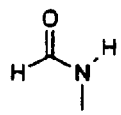
Figure 2:
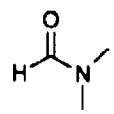
Figure 2:
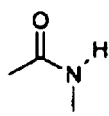
Figure 2:
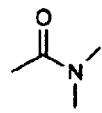
Figure 2:
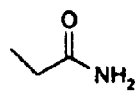
Figure 2:
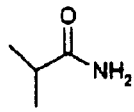

The additives tested can be divided into 4 subclasses. These are the pyrrolidones, the formamides, the acetamides and the higher-chain primary amides. FIG. 2 lists the additives by class and provides their structures and abbreviated nomenclatures.

For the N-WASP target, additives were initially tested at a few disparate concentrations using an annealing temperature gradient of 38–56° C. The result was that for all the additives tested the optimal annealing temperature (yield and specificity) was 41° C.; concentration did not influence the optimal annealing temperature. The relatively low value (41° C.) for the optimal annealing temperature is consistent with the findings that both formamide and NMP lower template melting temperature (12). Additives were then run at a spectrum of concentrations using an annealing temperature of 41° C., and the results in each case compared. The standard concentrations tested were: 0.5%, 1.0%, 1.5%, 2.0%, 2.5%, 3.0%, 5.0% and 1M. In the cases of formamide, 2-pyrrolidone and HEP additional concentrations were tested: 3.5%, 4.0%, and 4.5% for formamide and 6.0%, 7.0% and 7.5% for 2-pyrrolidone and HEP (see below). MMA and isobutyramide were only tested at regular incremental concentrations up to 3.0%, and then at 1M.

Before presenting the results, it is necessary to define precisely two terms that are central to our investigation. The potency of an additive is defined as the maximum densitometric volume of target band amplification observed at any concentration of that additive. Potencies of the additives were normalized to that of formamide, which was assigned a value of 1. The specificity of an additive is inversely related to the volume of secondary undesirable bands, and is quantitatively defined as the ratio of target band volume to the total volume of all bands, expressed as a percent. With the additives we tested, the highest specificity invariably occurred at a concentration where the volume of the target band was also at its maximum. The data in its entirety (results of PCR amplification for each additive at each concentration tested) is too extensive to present here. Potencies and best specificities of the additives are tabulated in Table 1.

TABLE 1

Potency, specificity and effective range of additives (N-WASP)

| Additive | Potency[1] | Specificity[2] | Effective Range (molar) | |
|---|---|---|---|---|
| | | | Leveling-off | Cutoff |
| 2-Pyrrolidone | 1.18 | 86% | 0.12 | 0.88 |
| HEP | 0.98 | 79% | 0.08 | >0.58, <1.0 |
| NMP | 1.10 | 81% | 0.15 | >0.51, <1.0 |
| Formamide | 1.00 | 87% | 0.67 | 0.89 |
| MMF | 1.07 | 79% | 0.51 | >0.84, <1.0 |
| DMF | 0.98 | 77% | 0.41 | >0.55, <1.0 |
| Acetamide | 1.07 | 98% | 0.25 | >0.84, <1.0 |
| MMA | 0.81 | 85% | 0.27 | >0.41, <1.0 |
| DMA | 0.88 | 80% | 0.29 | >0.57, <1.0 |
| Propionamide | 1.13 | 82% | 0.21 | >0.68, <1.0 |
| Isobutyramide | 1.10 | 85% | 0.23 | >0.35, <1.0 |
| Control | negligible | NA | NA | NA |

[1]Normalized densitometric volume of target band averaged over effective range: formamide = 1.
[2]Represents best specificity (densitometric volume of target as percent of total volume) over the effective range.

Analysis of the entire body of data generated with N-WASP reveals a number of interesting common features shared by all the additives. The first is that in the case of each additive there exists a range of concentrations over which the amplification is maximal. We term this phenomenon leveling-off; after a certain concentration (up to a point, as we will see below) the amplification levels off at its maximum value. Quantitation of the densitometric volumes of target band amplification over the leveled-off range showed that the volumes fall within +/−5% of the average values. The leveling-off concentration for each additive corresponds to the concentration of highest specificity, and hence to its optimal concentration, except for MMA which showed optimal performance at a concentration higher than its leveling-off concentration. Leveling-off data for the various additives are listed in Table 1. A second characteristic shared by all of the additives is that specificity decreases with increasing concentration. The third common feature has only begun to be investigated at this point. We refer to this characteristic as cutoff. For the N-WASP gene, all the additives display complete absence of amplification at 1M concentration. For formamide and 2-pyrrolidone, the location of cutoff was precisely determined and found to correspond to about 0.9M concentration in each case. Formamide exhibited drastically lower amplification at 5.0%, and was subsequently tested at 3.5%, 4.0% and 4.5%, whereupon cutoff was observed at 4.0% (0.89M). 2-pyrrolidone was tested at 6.0%, 7.0% and 7.5% concentration, and cutoff was observed at 7.5% (0.88M). In the cases of the other additives, cutoff occurs somewhere between 5.0% and 1M (between 3.0% and 1M in the cases of MMA and isobutyramide, 7.5% and 1M in the case of HEP). Cutoff data for the various additives are shown in Table 1. The concentration 0.9M falls within the cutoff interval for each of the additives, and in the cases of acetamide and MMF the intervals are sufficiently narrow to establish the cutoff at approximately 0.9M. The data thus appear to suggest that, in the case of N-WASP, cutoff occurs universally for low molecular-weight amides at around 0.9M.

In addition to N-WASP, three other targets—a 996 bp segment of the human c-jun gene, a 511 bp segment of the human prostate-specific membrane antigen (PSM) gene, and the bovine brain glycolipid transfer protein (GTP) gene (660 bp)—were studied to a limited extent to generalize our findings. These targets were selected because they were especially difficult to amplify in the absence of additives, due to their particularly high GC contents: c-jun, 64% GC; PSM, 52% GC with a 73% GC 158 bp region; GTP, 58% GC (13). We chose 2-pyrrolidone and acetamide, the two additives that performed best in the case of N-WASP, and the standard additive formamide for these studies. Even in the presence of the additives, these targets could not be amplified at denaturing temperatures below 95° C. Accordingly, denaturing was carried out at 95° C. rather than 92° C. for each. As in the case of N-WASP, the targets were initially tested at a few concentrations over an annealing temperature gradient (44–58° C.), and then at varying concentrations at their optimal annealing temperatures (50° C. for c-jun and PSM, 54° C. for GTP). Densitometric data are collected in Table 2. The study of these targets also displayed the phenomena of leveling-off and cutoff concentrations for the additives tested.

(660 bp). cDNA synthesis was carried out using the First-Strand RT-PCR kit from Stratagene on the respective mRNAs obtained from Clontech. All amplifications for each template were carried out using a single master batch of cDNA. Taq polymerase and dNTPs were purchased from Stratagene. Primers were obtained from Genosys. The sequences of the primers were:

c-jun primer j1: d(ATGACTGCAAAGATGGAAACG) (SEQ ID NO:3),
   primer j2: d(TCAAAATGTTTGCAACTGCTGCG) (SEQ ID NO:4);
PSM primer p1: d(AAACACTGCTGTGGTGGA) (SEQ ID NO:5),
   primer p2: d(TAGCTCAACAGAATCCAGGC) (SEQ ID NO:6);
GTP primer g1: d(GAATTCGAAATGGCGCTGCTGG) (SEQ ID NO:7),
   primer g2: d(CTCGAGGTCCAGAGTACCCGCTGTG) (SEQ ID NO:8).

Primer melting temperatures ($T_m$s) were calculated using the Genosys oligo calculator program. Calculated $T_m$s of the

TABLE 2

Potency and specificity of select additives (GTP, PSM, c-jun)[1,2]

| Additive | GTP Potency | GTP Specificity | PSM Potency | PSM Specificity | c-jun Potency | c-jun Specificity |
|---|---|---|---|---|---|---|
| Control | 0.38 | 20% | 0.88 | 29% | 0 | NA |
| Formamide | 1.00 | 100% | 1.00 | 83% | 1.00 | 100% |
| 2-Pyrrolidone | 1.37 | 100% | 2.62 | 83% | 2.90 | 100% |
| Acetamide | 0.53 | 100% | 0.95 | 66% | 0.99 | 100% |

[1]Determined at optimal concentrations of additives - formamide: 0.6M for PSM and 0.8M for GTP and c-jun; 2-pyrrolidone: 0.4M for all targets; acetamide: 0.8M for all targets.
[2]Specificity = densitometric volume of target band as percent of total volume.

EXAMPLE 2

Enhancement of Polynucleotide Amplification by Low Molecular Weight Sulfones

This example reports the results of an investigation of the effects of a novel class of compounds, the low molecular-weight sulfones, on the amplification of GC-rich templates. Sulfones are similar to sulfoxides with the important difference that the sulfur atom is double-bonded to two oxygen atoms, instead of one. Given the effectiveness of DMSO in PCR optimization, we were interested in determining whether these related compounds are also effective, and whether they offer any selective advantages in the cases of high-GC amplicons. The study incorporated three high-GC targets and examined the following compounds: methyl sulfone, ethyl sulfone, n-propyl sulfone, tetramethylene sulfone (sulfolane), butadiene sulfone (sulfolene), 2,4-dimethylsulfolane, DMSO and betaine. We consider structure-activity correlations in the class of low molecular-weight sulfones and identify several of these compounds as effective enhancers of GC-rich template amplification.

Materials and Methods

Polymerase chain reactions were carried out under the following conditions: 10 mM Tris-HCl (pH 8.8), 50 mM KCl, 1.5 mM MgCl2, 0.01% (w/v) gelatin, 0.2 uM primers, 0.06 ng/ul template, 0.2 mM each dNTP, 0.04 U/ul Taq polymerase. The templates used were a 996 bp segment of human myeloid leukocyte c-jun cDNA, a 511 bp segment of human prostate-specific membrane antigen (PSA) cDNA, and bovine brain glycolipid transfer protein (GTP) cDNA primers were as follows: j1-63.9° C., j2-70.8° C., p1-60.3° C., p2-61.9° C., g1-73.3° C., g2-74.4° C.

Additive compounds were purchased from the following sources. Methyl sulfone, ethyl sulfone, n-propyl sulfone, n-butyl sulfone, tetramethylene sulfone (sulfolane), 2,4-dimethylsulfolane and butadiene sulfone (sulfolene) were acquired from Acros. DMSO was obtained from Fluka. Betaine was purchased from Sigma.

Amplification reactions were carried out on a Robocycler Gradient 96 thermal cycler from Stratagene using 50 ul solutions in 200 ul thin-walled tubes. Before the addition of Taq polymerase, a hotstart procedure was conducted that consisted of an initial cycle of 95° C. for 5 minutes (Ivinson et al., 1991) to ensure complete first-strand separation, followed by a cycle of 54° C. for 5 minutes. Amplifications were run for 30 cycles. Denaturation was done for 1 minute at 92° C. for PSM and GTP, the minimum temperature that yielded discemable amplification of these targets in the presence of additives, and at either 92° C. or 95° C. for d-jun. Extension was done at 72° C. for 1 minute. Annealings were carried out either at fixed concentrations of additives using a temperature gradient of 44–58° C. or at varying concentrations of additives using fixed temperatures of 48° C. for PSM, 50° C. for GTP, and 50° C. or 53° C., depending on the additive, for c-jun.

Electrophoresis of amplification products was done on 0.8% agarose gels in which 20 ul reaction products were loaded with 4 ul loading buffer. Gels were run at 60V for 80 minutes, stained with ethidium bromide, visualized on a UV transilluminator (Fisher), and documented by Polaroid photography. Quantitation of amplification products was carried out using an ImageScanner densitometer and ImageMaster Total Lab software from Amersham Pharmacia Biotech. Background correction was conducted using the software's rolling disc method. Data were plotted using the Kaleida Graph application from Synergy Software. Interpolation of data points at intermediate concentrations was carried out using the software's cubic spline method.

Results

Figure 3:
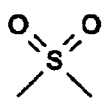
FIG. 3. Structures of certain sulfones tested for enhancement of polymerase chain reaction, as described in Example 2. Common names used herein are indicated in parentheses.
Figure 3:
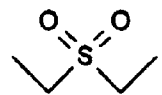
Figure 3:
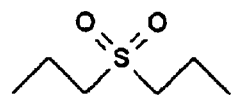
Figure 3:
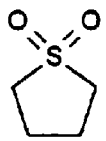
Figure 3:
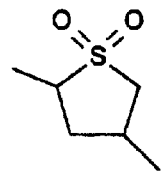
Figure 3:

The effects of sulfone additives on PCR amplification were studied in this work using three different GC-rich templates. Description of the effectiveness of the various additives was achieved in the case of each target through the assignment of two densitometric quantities, termed potency and specificity as describe above, to each compound. The potency of an additive is defined as the maximum densitometric volume of target band amplification over the concentration gradient tested for that additive. Maximal target band volumes were interpolated from the data sets by fitting cubic splines to the data. Potencies of the various compounds tested were normalized to that of DMSO (except where it failed to perform), which was assigned a value of 1. The specificity of an additive at a particular concentration is defined as the ratio of the volume of target band amplification to the total volume of all bands, including undesired nonspecific bands, expressed as a percent. In addition to these densitometric quantities, a third characteristic value, the effective range, was assigned to each compound in the case of each target. The effective range of an additive was defined as the interval of concentrations, determined from the additive's cubic spline curve, over which the volume of target band amplification is at least 50% of the maximal volume. The structures of the additives examined in this work are displayed in FIG. 3. Since a major focus of this study was to determine structure activity correlations in the sulfone family, the group of compounds was chosen to include the simplest n-alkyl sulfones and the simple cyclic sulfone, sulfolane. In addition, a ring-substituted cyclic sulfone (2,4-dimethylsulfolane) and a cyclic alkene sulfone (sulfolene) were included to study the effects of these structural modifications on amplification. n-Butyl and higher alkyl sulfones were omitted because of their low water solubilities. For the sake of comparison, dimethylsulfoxide (DMSO) and betaine were included in the investigation. DMSO is the most widely-used additive in PCR reactions, and is commonly considered to be one of the most effective and versatile additives. Betaine has been described as a particularly potent enhancer of high-GC template amplification.

A 996 bp segment of human myeloid leukocyte c-jun cDNA (64% GC) was selected as the central target for this investigation because of its particularly high GC content and because it was impossible to amplify in the absence of additives (See Example 1). Even in the presence of additives, a 95° C. denaturing temperature was necessary in almost every case for discernable amplification. Each of the additives was initially tested with c-jun at a few evenly-spaced concentrations over a 44–58° C. annealing temperature gradient, using a conventional denaturing temperature of 92° C. The only compound that yielded discernable amplification under these denaturing conditions was sulfolane. None of the other additives tested—DMSO, betaine, or the other sulfones—showed any amplification. Next, a denaturing temperature of 95° C. was employed in order to examine the capabilities of the other compounds in amplifying c-jun under less stringent conditions. Again, each additive was tested over a 44–58° C. annealing temperature gradient, at a few concentrations that were chosen to provide a rough perception of the effective range of the compounds and also to determine whether the optimal annealing temperature is sensitive to additive concentration. It was found that the optimal annealing temperature of each compound, except betaine, was 50° C. and did not depend on concentration. In the case of betaine, the optimal annealing temperature was 53° C. n-Propyl sulfone and dimethylsulfolane were found to be ineffective at any of the concentrations tested in these initial screenings, and were omitted from further studies. Each remaining additive was subsequently tested over a range of closely spaced molar concentrations at their optimal annealing temperatures. These concentrations, chosen partly on the basis of the concentrations that were effective in the initial screenings, were as follows: methyl sulfone—0.2 to 1.0M at 0.1M intervals; ethyl sulfone—0.2, 0.3, 0.4M; sulfolane—0.05M and 0.1 to 0.7M at 0.1M intervals; sulfolene—0.05M and 0.1 to 0.4M at 0.1M intervals, DMSO—0.2 to 1.9M at 0.1M intervals; betaine—0.3 to 1.0M at 0.1M intervals and 1.5 to 3.0M at 0.5M intervals.

Results are shown in Table 3. The additives that performed best in the c-jun studies—methyl sulfone, sulfolane and DMSO—were chosen for additional studies using two more DNA targets: a 511 bp segment of human prostate specific membrane antigen (PSM) cDNA and bovine brain glycolipid transfer protein (GTP) cDNA (660 bp). These targets were also very difficult to amplify (Henke et al, 1997) due to their high GC contents: PSM, 52% GC with a 73% GC 158 bp region; GTP, 58% GC. In addition, their amplification is generally accompanied by the amplification of nonspecific bands. Betaine was also included in this phase of the investigation, but was only tested against one template, PSM, due to its poorer performance with c-jun (Table 3). As in the case of c-jun, the additives were first tested at a few concentrations over an annealing temperature gradient of 44–58° C., and then at various concentrations at their optimal annealing temperatures (48° C. for PSM, 50° C. for GTP). A 92° C. denaturing temperature was used in all experiments.

TABLE 3

Potency and effective range of additives (c-jun)

| Additive | 92° C. denaturing Potency[a] | 95° C. denaturing | |
|---|---|---|---|
| | | Potency[b] | Effective Range[c] (M) |
| Sulfolane | 1.00 | 1.10 | 0.15–0.40 |
| Sulfolene | 0.00 | 0.17 | 0.15–0.27 |
| Dimethylsulfolane | 0.00 | 0.00 | NA |
| Methyl sulfone | 0.00 | 0.85 | 0.57–1.03 |
| Ethyl sulfone | 0.00 | 0.20 | 0.15–0.33 |
| Propyl sulfone | 0.00 | 0.00 | NA |
| DMSO | 0.00 | 1.00 | 0.36–1.53 |
| Betaine | 0.00 | 0.52 | 0.88–1.41 |
| Control | 0.00 | 0.00 | NA |

[a]Normalized maximum densitometric volume of target band: sulfolane = 1.
[b]Normalized maximum densitometric volume of target band: DMSO = 1.
[c]Concentration interval over which densitometric volume of target is at least 50% of maximum volume.

Potencies, best specificities and effective ranges of the additives tested in the case of these additional targets are shown in Table 4. The additive concentration that yielded the maximum target band amplification was found in each case to display a specificity that was within 2% of the best specificity.

TABLE 4

Potency[a], specificity[b] and effective range[c] of select additives (PSM, GTP)

| | PSM | | | GTP | | |
|---|---|---|---|---|---|---|
| Additive | Potency | Specificity | Range (molar) | Potency | Specificity | Range (molar) |
| Sulfolane | 1.64 | 93% | 0.25–0.50 | 3.30 | 100% | 0.18–0.55 |
| Methyl sulfone | 1.40 | 91% | 0.85–1.15 | 1.06 | 100% | 0.65–1.20 |
| DMSO | 1.00 | 88% | 0.73–1.35 | 1.00 | 89% | 0.75–1.25 |
| Betaine | 0.21 | 34% | NA | NA | NA | NA |
| Control | 0.21 | 34% | NA | 0.06 | 53% | NA |

[a]Normalized maximum densitometric volume of target band: DMSO = 1.
[b]Best specificity (densitometric volume of target as percent of total volume) over the effective range.
[c]Concentration interval over which densitometric volume of target is at least 50% of maximum volume.

EXAMPLE 3

Enhancement of Polynucleotide Amplification by Low Molecular Weight Sulfoxides Examples 1 and 2 set forth results of thorough investigations of the effects of low molecular-weight amides and low molecular-weight sulfones on the amplification of GC-rich targets. In those examples, 2-pyrrolidone and sulfolane were shown to be especially effective enhancers of amplification. In this example, several other water soluble sulfoxides were tested to determine whether these compounds are also effective. The study incorporated three GC-rich amplicons and examined the following compounds: dimethyl sulfoxide (DMSO), methyl secbutyl sulfoxide, n-propyl sulfoxide, n-butyl sulfoxide and tetramethylene sulfoxide. We identify certain of these compounds as effective enhancers of high-GC template amplification, compare their effectiveness to those of the related sulfones, and consider structure-activity correlations in the enhancement of PCR by sulfur-oxygen compounds. We introduce tetramethylene sulfoxide as an exceptionally potent PCR enhancer.

Materials and Methods

Polymerase chain reactions were conducted as described above on a Robocycler Gradient 96 thermal cycler from Stratagene using 50 ul solutions in 200 ul thin-walled tubes. Prior to the introduction of Taq polymerase, a hotstart protocol was followed that consisted of an initial cycle of 95° C. for 5 minutes (6) to ensure complete first-strand separation, followed by a cycle of 54° C. for 5 minutes. Amplifications were run for 30 cycles under the following conditions: 10 mM Tris-HCl (pH 8.8), 50 mM KCl, 1.5 mM MgCl2, 0.01% (w/v) gelatin, 0.2 uM primers, 0.06 ng/ul template, 0.2 mM each dNTP, 0.04 U/ul Taq polymerase. In order to facilitate comparison with the related sulfone additives, the templates studied were identical to those used in (4): bovine brain glycolipid transfer protein (GTP) cDNA (660 bp), a 996 bp segment of human myeloid leukocyte c-jun cDNA, and a 511 bp segment of human prostate-specific membrane antigen (PSM) cDNA. The sequences of the primers were as set forth in Example 2.

Denaturation was conducted for 1 minute at 92° C. for PSM and GTP, the minimum temperature that afforded discernable amplification of these targets in the presence of additives, and at either 92° C. or 95° C. for c-jun. Extension was carried out at 72° C. for 1 minute. Annealings were done either at fixed concentrations of additives using a temperature gradient of 48–62° C. or at varying concentrations of additives using fixed temperatures. These temperatures were, depending on the additive: 50° C., 58° C. or 60° C. for GTP; 48° C. or 52° C. for PSM; and 50° C. for c-jun.

Taq polymerase and dNTPs were acquired from Stratagene. Primers were obtained from Genosys. Additive compounds were acquired from the following vendors. n-Propyl sulfoxide, n-butyl sulfoxide and tetramethylene sulfoxide were obtained from Acros. Methyl sec-butyl sulfoxide was obtained from Lancaster Synthesis (Clariant). DMSO was purchased from Fluka.

Analysis of amplification products was carried out on 0.8% agarose gels. Quantitation of products was conducted using an ImageScanner densitometer and ImageMaster Total Lab software from Amersham Pharmacia Biotech.

Results

Figure 4:
FIG. 4. Structures of certain sulfoxides tested for enhancement of polymerase chain reaction, as described in Example 3.
Figure 4:
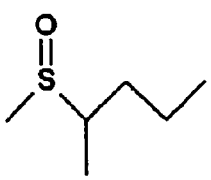
Figure 4:
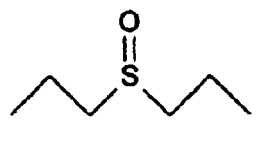
Figure 4:
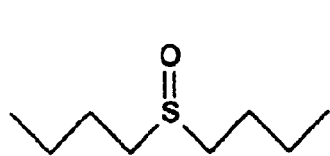
Figure 4:
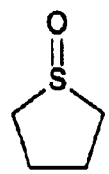

The structures of the sulfoxides that were studied in this investigation are displayed in FIG. 4. All known water-soluble symmetrical n-alkyl sulfoxides were tested, with the exception of ethyl sulfoxide, which was not readily available from known chemical sources. Methyl sec-butyl sulfoxide, which has a total number of carbons between those of ethyl and propyl sulfoxides, was used instead. This was the only unsymmetrical sulfoxide studied in this work. Tetramethylene sulfoxide, a simple cyclic sulfoxide, was also included in the study to examine the effects of the ring structure on amplification.

In the case of each of the templates studied in this work, the effects the various additives on PCR amplification were assessed through the assignment of two densitometric quantities to each of the compounds. As above, potency was defined as the maximum densitometric volume of the target band observed at any concentration of an additive. Specificity was defined as the ratio of target band volume to the total volume of all bands, including nonspecific bands, expressed as a percent. Effective range of an additive was defined as the range of concentrations over which the volume of target band amplification is greater than or equal to 50% of its maximal value.

Three high-GC templates were used in this study to determine the effects of sulfoxide additives on PCR amplification. Of these, bovine brain glycolipid transfer protein (GTP) cDNA (660 bp, 58% GC) was chosen as the primary target. The various additives were first tested with GTP at a few disparate concentrations over an annealing temperature gradient of 48–62° C., employing a 92° C. denaturing temperature. Butyl sulfoxide did not yield any detectable amplification, and was not included in subsequent studies. The remaining additives were then tested over molar concentration gradients at their optimal annealing temperatures (60° C. for tetramethylene sulfoxide and propyl sulfoxide, 58° C. for methyl sec-butyl sulfoxide and 50° C. for DMSO). The concentrations were selected partly on the basis of which concentrations were effective in the temperature gradient experiments. These concentrations were: DMSO—0.2, 0.3, 0.5,0.7,0.9, 1.2, 1.4M; methyl sec-butyl sulfoxide—0.1, 0.2, 0.25, 0.3, 0.35, 0.4M; propyl sulfoxide—0.1, 0.2, 0.3, 0.4M; tetramethylene sulfoxide—0.1, 0.2, 0.3, 05, 0.7, 0.9, 1.2M. The potencies, best specificities and effective ranges displayed by the additives in the GTP studies are shown in Table 5.

TABLE 5

Potency[a], specificity[b] and effective range[c] of additives (GTP)

| Additive | Potency | Specificity | Effective range (molar) |
|---|---|---|---|
| Tetramethylene sulfoxide | 3.68 | 100% | 0.28–1.00 |
| Propyl sulfoxide | 2.82 | 100% | 0.15–0.36 |
| Methyl sec-butyl sulfoxide | 3.33 | 100% | 0.03–0.31 |
| Butyl sulfoxide | 0.06 | 53% | NA |
| DMSO | 1.00 | 89% | 0.75–1.25 |
| Control | 0.06 | 53% | NA |

[a]Normalized maximum densitometric volume of target band: DMSO = 1.
[b]Best specificity (densitometric volume of target as percent of total volume) over the effective range.
[c]Concentration interval over which densitometric volume of target is at least 50% of maximum volume.

The symmetrical sulfoxide series—DMSO, propyl sulfoxide and tetramethylene sulfoxide—was next tested with two additional GC-rich targets: a 996 bp region of human myeloid leukocyte c-jun cDNA (64% GC) and a 511 bp segment (52% GC with a 158 bp 73% GC region) of human prostate-specific membrane antigen (PSM) cDNA. The asymmetrical compound methyl sec-butyl sulfoxide was not tested with these targets. In the absence of additives, amplification of c-jun is impossible; amplification of PSM is weak and accompanied by amplification of nonspecific bands.

As before, the compounds were first tested with these templates at a few different concentrations over a 48–62° C. annealing temperature gradient, using a conventional 92° C. denaturing temperature. In the case of c-jun, only tetramethylene sulfoxide gave discernable amplification at this denaturing temperature. In order to study the abilities of the other compounds to enhance c-jun amplification under less stringent conditions, the c-jun screenings were repeated employing a 95° C. denaturing temperature, whereupon all three additives were found to be effective. With PSM, both DMSO and tetramethylene sulfoxide were effective in enhancing amplification under 92° C. denaturing conditions. Using a denaturing temperature of 92° C. for c-jun and 95° C. for PSM, the effective additives were then tested at various concentrations at their best annealing temperatures –50° C. for all additives with c-jun; 52° C. and 48° C. for tetramethylene sulfoxide and DMSO, respectively, with PSM. The potencies, best specificities and effective ranges of the additives for c-jun and PSM are listed in Tables 6 and 7.

TABLE 6

Potency and effective range of select additives (c-jun)

| Additive | 92° C. denaturing Potency[a] | 95° C. denaturing Potency[b] | Effective Range[c] (molar) |
|---|---|---|---|
| Tetramethylene sulfoxide | 1.00 | 1.18 | 0.19–0.55 |
| Propyl sulfoxide | 0.00 | 0.25 | 0.08–0.22 |

TABLE 6-continued

Potency and effective range of select additives (c-jun)

| Additive | 92° C. denaturing Potency[a] | 95° C. denaturing Potency[b] | Effective Range[c] (molar) |
|---|---|---|---|
| DMSO | 0.00 | 1.00 | 0.36–1.53 |
| Control | 0.00 | 0.00 | NA |

[a]Normalized maximum densitometric volume of target band: tetramethylene sulfoxide = 1.
[b]Normalized maximum densitometric volume of target band: DMSO = 1.
[c]Concentration interval over which densitometric volume of target is at least 50% of maximum volume.

TABLE 7

Potency[a], specificity[b] and effective range[c] of select additives (PSM)

| Additive | Potency | Specificity | Effective Range (molar) |
|---|---|---|---|
| Tetramethylene sulfoxide | 1.74 | 93% | 0.33–0.68 |
| Propyl sulfoxide | 0.21 | 34% | NA |
| DMSO | 1.00 | 88% | 0.73–1.35 |
| Control | 0.21 | 34% | NA |

[a]Normalized maximum densitometric volume of target band: DMSO = 1.
[b]Best specificity (densitometric volume of target as percent of total volume) over the effective range.
[c]Concentration interval over which densitometric volume of target is at least 50% of maximum volume.

Representative results from experiments testing sulfones (Example 2) and sulfoxides (this Example) for PCR enhancement are set forth in Table 8.

TABLE 8

Representative results from sulfoxide and sulfone PCR enhancement studies

| | I. GTP | | II. c-jun 95° C. denaturing | III. c-jun 92° C. denaturing |
|---|---|---|---|---|
| Additive | Potency[a] | Range[b] (molar) | Potency[a] | Potency[c] |
| DMSO | 1.00 | 0.75–1.25 | 1.00 | 0.00 |
| Methyl sulfone[d] | 1.06 | 0.65–1.20 | 0.85 | 0.00 |
| Methyl sec-butyl sulfoxide | 3.33 | 0.03–0.31 | NA | 0.00 |
| Ethyl sulfone | NA | NA | 0.20 | 0.00 |
| Propyl sulfoxide | 2.82 | 0.15–0.36 | 0.25 | 0.00 |
| Propyl sulfone[d] | NA | NA | 0.00 | 0.00 |
| Butyl sulfoxide | 0.00 | NA | 0.00 | 0.00 |
| Tetramethylene sulfoxide | 3.68 | 0.28–1.00 | 1.18 | 3.02 |
| Sulfolane[d] | 3.30 | 0.18–0.55 | 1.10 | 1.00 |
| Betaine[d] | NA | NA | 0.52 | 0.00 |

[a]Normalized maximum densitometric volume of target band: DMSO = 1.
[b]Concentration interval over which densitometric volume of target is at least 50% of maximum volume
[c]Normalized maximum densitometric volume of target band: sulfolane = 1.

The present invention is not limited to the embodiments described and exemplified above, but is capable of variation and modification within the scope of the appended claims.

We claim:

1. A composition for performing a polynucleotide replication reaction, which comprises a buffer, one or more template polynucleotides, nucleotide triphosphates, one or more polymerase enzymes or fragments thereof, and one or more reaction adjuvants comprising compounds of the formula:

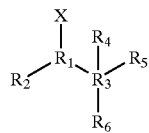

Formula I wherein:

$R_1$ is C or S; and
when $R_1$ is C, X is =O, $R_3$ is N and $R_6$ is absent;
when $R_1$ is S, X is =O or

and $R_3$ is C;

$R_2$ is H or $CH_3$ only when one or more of $R_4$, $R_5$ and $R_6$ is not H, and otherwise $R_2$ is an unsubstituted or halogen-, hydroxy- or alkoxy- substituted alkyl or cycloalkyl of length m, wherein m is selected such that the total number of carbons in the compound is between 3 and 8 when $R_1$ is C and between 2 and 8 when $R_1$ is S; wherein any two of $R_2$, $R_3$, $R_4$, $R_5$ and $R_6$ optionally form a cyclic structure in which cyclization is effected through a bond between them; and $R_4$, $R_5$ and $R_6$ each is H, alkyl, cycloalkyl or halogen-, hydroxy- or alkoxy- substituted alkyl or cycloalkyl of length n, wherein n is selected such that the total number of carbons in the compound is between 3 and 8 when $R_1$ is C and between 2 and 8 when $R_1$ is S and when $R_4$ and $R_5$ are $CH_3$, $R_2$ cannot be H or $CH_3$.

2. The composition of claim 1, wherein the reaction adjuvant comprises a cyclic compound, wherein the cyclization is effected through a bond between any two of $R_2$, $R_3$, $R_4$, $R_5$ and $R_6$.

3. The composition of claim 2, wherein the cyclic portion of the compound comprises five, six or seven members.

4. The composition of claim 3, wherein $R_1$ is S and remainder of the compound is unsubstituted.

5. The composition of claim 1, wherein the reaction adjuvant comprises a compound in which $R_1$ is S, X is =O or

and $R_3$ is C.

6. The composition of claim 5, wherein the compound is cyclic.

7. The composition of claim 6, wherein the cyclic structure of the compound is a five, six, or seven-membered ring formed by a bond between $R_2$ and either $R_4$, $R_5$ or $R_6$.

8. The composition of claim 7, wherein the ring is unsubstituted except in $R_1$.

9. The composition of claim 8, wherein the compound is selected from the group consisting of tetramethylene sulfone and tetramethylene sulfoxide.

10. The composition of claim 5, wherein the compound is acyclic.

11. The composition of claim 10, comprising a compound in which $R_2$ or $R_3$ is lower alkyl or substituted lower alkyl.

12. The composition of claim 11, wherein the compound is selected from the group consisting of methyl sulfone, ethyl sulfone, n-propyl sulfone, n-propyl sulfoxide and methyl sec-butyl sulfoxide.

13. The composition of claim 1, wherein the polynucleotide replication reaction is an amplification reaction.

14. The composition of claim 13, wherein the amplification reaction is selected from the group consisting of polymerase chain reaction, nucleic acid sequence-based amplification, transcription-based amplification system, self-sustained sequence replication, ligation amplification reaction, Q-beta replicase amplification and ligase chain reaction.

15. The composition of claim 1, wherein the one or more polymerases or fragments thereof is selected from the group consisting of Taq polymerase, Tth polymerase, Tme polymerase, Tli polymerase, Pfu polymerase, DNA polymerase I, Klenow fragment and reverse transcriptase.

16. The composition of claim 5, wherein the reaction adjuvant has a potency of at least 75% of the potency of DMSO or formamide in an equivalent polynucleotide chain reaction (PCR).

17. The composition of claim 1, wherein the reaction adjuvant has a specificity of at least 80% of the specificity of DMSO or formamide in an equivalent polynucleotide chain reaction (PCR).

18. The composition of claim 1, wherein the reaction adjuvant has an effective range spanning at least 0.1 M.

19. The composition of claim 1; wherein the polynucleotide template comprises greater than 50% G+C.

20. A kit for performing a polynucleotide amplification reaction, comprising a container that includes:

a) one or more compounds of the formula:

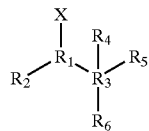

Formula I wherein:

$R_1$ is C or S; and
when $R_1$ is C, X is =O, $R_3$ is N and $R_6$ is absent;
when $R_1$ is S, X is =O or

and $R_3$ is C;

$R_2$ is H or $CH_3$ only when one or more of $R_4$, $R_5$ and $R_6$ is not H, and otherwise $R_2$ is an unsubstituted or halogen-, hydroxy- or alkoxy- substituted alkyl or cycloalkyl of length m, wherein m is selected such that the total number of carbons in the compound is between 3 and 8 when $R_1$ is C and between 2 and 8 when $R_1$ is S; wherein any two of $R_2$, $R_3$, $R_4$, $R_5$ and $R_6$ can form a cyclic structure in which cyclization is effected through a bond between them; and $R_4$, $R_5$ and $R_6$ each is H, alkyl, cycloalkyl or halogen-, hydroxyl or alkoxy- substituted alkyl or cycloalkyl of length n, wherein n is selected such that the total number of carbons in the compound is between 3 and 8 when $R_1$ is C and between 2 and 8 when $R_1$ is S; and when $R_4$ and $R_5$ are $CH_3$, $R_2$ cannot be H or $CH_3$, and b) instructions for using the one or more compounds in a polynucleotide replication reaction.

21. The kit of claim 20, which further comprises one or more of:

a) a polynucleotide replication reaction buffer;
b) nucleotide triphosphates;
c) oligonucleotide primers;
d) a known template polynucleotide for use as a control; and
e) one or more polymerase enzymes.

22. The kit of claim 21, customized for performing amplification reactions.

23. The kit of claim 22, customized for performing PCR.

24. A kit for performing a method for optimizing a polynucleotide replication reaction for a selected polynucleotide, which comprises a container in which is included:

a) a plurality of reaction adjuvants comprising compounds of the formula:

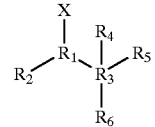

Formula I wherein $R_1$ is C or S; and
when $R_1$ is C, X is =O, $R_3$ is N and $R_6$ is absent;
when $R_1$ is S, X is =O or

and $R_3$ is C;

$R_2$ is H or $CH_3$ only when one or more of $R_4$, $R_5$ and $R_6$ is not H, and otherwise $R_2$ is an unsubstituted halogen-, hydroxy- or alkoxy- substituted alkyl or cycloalkyl of length m, wherein m is selected such that the total number of carbons in the compound is between 3 and 8 when $R_1$ is C and between 2 and 8 when $R_1$ is S; wherein any two of $R_2$, $R_3$, $R_4$, $R_5$ and $R_6$ optionally form a cyclic structure in which cyclization is effected through a bond between them; and $R_4$, $R_5$, and $R_6$ each is H, alkyl, cycloalkyl or halogen-, hydroxy- or alkoxy- substituted alkyl or cycloalkyl of length n, wherein n is selected such that the total number of carbons in the compound is between 3 and 8 when $R_1$ is C and between 2 and 8 when $R_1$ is S; and when $R_4$ and $R_5$ are $CH_3$, $R_2$ cannot be H or $CH_3$ and b) instructions for using the reaction adjuvants to optimize polynucleotide replication of a selected template polynucleotide.

25. The kit of claim 24, which further comprises one or more of:

a) a polynucleotide replication reaction buffer;
b) nucleotide triphosphates;
c) oligonucleotide primers;
d) a known template polynucleotide for us as a control;
e) one or more polymerase enzymes; and
f) one or more reaction vessels for performing the plurality of polynucleotide replication reactions.

26. The kit of claim 25, customized for performing amplification reactions.

27. The kit of claim 26, customized for performing PCR.

28. The composition of claim 12, wherein the reaction adjuvant has a potency of at least 75% of the potency of DMSO or formamide in an equivalent polynucleotide chain reaction (PCR);
wherein the reaction adjuvant has a specificity of at least 80% of the specificity of DMSO or formamide in an equivalent polynucleotide chain reaction (PCR); and
wherein the reaction adjuvant has an effective range spanning at least 0.1 M.

29. The composition of claim 14, wherein the compound is tetramethylene sulfoxide.

30. The composition of claim 1, wherein the one or more polymerase or fragments thereof is selected from the group consisting of Taq polymerase, Tme polymerase, Pfu Polymerase, DNA polymerase I, Klenow fragment and reverse transcriptase.

* * * * *

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: Novel Sequence

<400> SEQUENCE: 1
atgagctccg gccagcagc                                                    19

<210> SEQ ID NO 2
<211> LENGTH: 27
<212> TYPE: DNA
<213> ORGANISM: Artificial Sequence
<220> FEATURE:
<223> OTHER INFORMATION: Novel Sequence

<400> SEQUENCE: 2
tcagtcttcc cattcatcat catcctc                                           27

<210> SEQ ID NO 3
<211> LENGTH: 21
<212> TYPE: DNA
<213> ORGANISM: Artificial Sequence
<220> FEATURE:
<223> OTHER INFORMATION: Novel Sequence

<400> SEQUENCE: 3
atgactgcaa agatggaaac g                                                 21

<210> SEQ ID NO 4
<211> LENGTH: 23
<212> TYPE: DNA
<213> ORGANISM: Artificial Sequence
<220> FEATURE:
<223> OTHER INFORMATION: Novel Sequence

<400> SEQUENCE: 4
tcaaaatgtt tgcaactgct gcg                                               23

<210> SEQ ID NO 5
<211> LENGTH: 18
<212> TYPE: DNA
<213> ORGANISM: Artificial Sequence
<220> FEATURE:
<223> OTHER INFORMATION: Novel Sequence

<400> SEQUENCE: 5
aaacactgct gtggtgga                                                     18

<210> SEQ ID NO 6
<211> LENGTH: 20
<212> TYPE: DNA
<213> ORGANISM: Artificial Sequence
<220> FEATURE:
<223> OTHER INFORMATION: Novel Sequence

<400> SEQUENCE: 6
tagctcaaca gaatccaggc                                                   20

<210> SEQ ID NO 7
<211> LENGTH: 22

```
<212> TYPE: DNA
<213> ORGANISM: Artificial Sequence
<220> FEATURE:
<223> OTHER INFORMATION: Novel Sequence

<400> SEQUENCE: 7
gaattcgaaa tggcgctgct gg                                    22

<210> SEQ ID NO 8
<211> LENGTH: 25
<212> TYPE: DNA
<213> ORGANISM: Artificial Sequence
<220> FEATURE:
<223> OTHER INFORMATION: Novel Sequence

<400> SEQUENCE: 8
ctcgaggtcc agagtacccg ctgtg                                 25
```